United States Patent [19]

Moulin et al.

[11] Patent Number: 5,922,655

[45] Date of Patent: Jul. 13, 1999

[54] MAGNESIUM LOW RATE NUMBER SULPHONATES

[75] Inventors: Dominique Moulin, N. D. de Gravenchon, France; John Arthur Cleverley; Charles Herbert Bovington, both of Oxfordshire, United Kingdom

[73] Assignee: Exxon Chemical Company, Linden, N.J.

[21] Appl. No.: 09/158,732

[22] Filed: Sep. 22, 1998

Related U.S. Application Data

[62] Division of application No. 08/875,247, filed as application No. PCT/EP96/00813, Feb. 27, 1996, Pat. No. 5,883,056.

[30] Foreign Application Priority Data

Feb. 28, 1995 [GB] United Kingdom .................. 9504033

[51] Int. Cl.⁶ ...................... C10M 159/24; C10M 159/12
[52] U.S. Cl. ......................... 508/390; 508/391; 508/398; 508/393
[58] Field of Search ................................. 508/390, 391, 508/398, 393

[56] References Cited

U.S. PATENT DOCUMENTS 4,764,295  8/1988  Le Coent .............................. 508/394

FOREIGN PATENT DOCUMENTS 1 575 957  10/1980  United Kingdom .

*Primary Examiner*—Jerry D. Johnson
*Attorney, Agent, or Firm*—Ohlandt, Greeley, Ruggiero & Perle

[57] ABSTRACT

Magnesium low base number (LBN) sulphonates derived from high molecular weight sulphonic acids have low viscosity and are chloride free. The magnesium low base number sulphonates are not skin sensitisers. In their preparation neutralisation of high molecular weight sulphonic acids or partially neutralised soaps of high molecular weight sulphonic acids is completed by the use of a high base number sulphonate in conjunction with a carboxylic acid. The process does not require the use of chloride containing promoters and produces low chloride products.

10 Claims, No Drawings

MAGNESIUM LOW RATE NUMBER SULPHONATES

This Application is a Divisional Application of application Ser. No. 08/875,247 filed on Sep. 10, 1997, now U.S. Pat. No. 5,883,056, a Section 371(a) USA National Phase Application based on PCT/EP96/00813 filed Feb. 27, 1996

The present invention relates to magnesium low base number magnesium sulphonates and to processes for the production of these sulphonates. The invention also relates to oil based compositions containing these magnesium low base number sulphonates.

Basic or neutral sulphonates may be used as additives in lubricating oils for petrol engines and diesel engines for example for vehicles or marine engines. Neutral and low base number sulphonates function primarily as detergents to keep engine surfaces clean. High base number sulphonates are primarily used to neutralise acids produced in the oil during use. These sulphonates may help to inhibit corrosion.

Neutral and low base number sulphonates for use as oil additives are usually prepared by the neutralisation of a sulphonic acid with a basic salt such as a metal oxide or hydroxide in a suitable diluent oil. The sulphonate product may be a mixture of a number of species. In addition dispersed metal hydroxide may be present.

The product of this process may display some basicity, for example if the basic salt is added in stoichiometric excess to that required for complete neutralisation of the sulphonic acid, or some other basic component is present. The product in this case is said to be overbased.

The neutral metal salts of typical sulphonic acids are extremely viscous materials and would have a TBN, as measured by ASTM D-2896, of zero. Methods have been sought which permit lower viscosity products to be prepared. This has been achieved by the incorporation of chloride, formate and hydroxide ions into the product. The products of these techniques are not truly neutral but are slightly overbased in that they contain more base than that required to react stoichiometrically with the sulphonic acid.

It is difficult to produce magnesium low base number magnesium sulphonates from any groups of sulphonic acids; moreover, it is particularly difficult to produce magnesium low base number magnesium sulphonates from synthetic sulphonic acids of medium to high molecular weight, ie synthetic acids of average molecular weights of 500 or greater, which also have low viscosity. High viscosity soaps or high viscosity sulphonates are produced which have a lower than expected base number and high sediment levels. Typically, a filtration or solid/liquid separation is required. The viscosity can be controlled to some extent by the addition of halide as outlined above.

U.S. Pat. No. 4,764,295 discloses a process for the production of low base number alkaline earth metal sulphonates from sulphonic acids which have alkyl radicals of $C_{15}$ to $C_{40}$; the process utilises chloride containing salts and carboxylic acids such as formic acid. The products have relatively low viscosity but contain chloride.

High base number sulphonates are generally prepared by a process of neutralisation with excess base (overbasing) followed by carbonation. Typically the sulphonic acid is neutralised with excess basic metal oxide or hydroxide in a suitable diluent. Some of the excess basic metal oxide or hydroxide is converted to metal carbonate via carbonation. Typically the reaction is carried out in the presence of hydrocarbon and/or polar solvents such as toluene methanol and diluent oil; some or all of these solvents may be subsequently removed. The resulting product is a colloidal dispersion, in a diluent oil, of sub-micron particles of basic magnesium carbonate which are sterically stabilised by the magnesium sulphonate species produced by the reaction.

Sulphonates have been prepared from synthetic sulphonic acids which have in turn been prepared for example by the sulphonation of $C_{12}$ to $C_{60+}$ alkyl substituted benzene, or xylene or toluene compounds and mixtures thereof. It has been found that some synthetic sulphonic acids are difficult to neutralise with for example magnesium hydroxide or lime to produce sulphonates which have acceptable properties; the attempted neutralisation results in the production of gelatinous products which for example are solid at room temperature. This is a particular problem when trying to prepare Neutral or Low Base Number Sulphonates from such sulphonic acids. Methods have been proposed to overcome this problem associated with synthetic sulphonic acids. One such method for sulphonic acids of molecular weight 480–540 is described in GB 1 575 957 wherein a large stoichiometric excess, over that required for neutralisation of the sulphonic acid, of alkaline earth metal hydroxide is added to a portion of the sulphonic acid in a diluent to produce a reaction mixture; the remainder of the sulphonic acid is subsequently added to the mixture, this addition being less than that which would be required to fully react with the remaining alkaline earth metal hydroxide in the mixture. In addition a solution containing a source of chloride ion is added to the mixture after, eg calcium hydroxide or lime addition, the chloride ion is believed to act as a fluidiser for the product formation and is beneficial in enabling the production of fluid, filterable products from certain sulphonic acids such as synthetic sulphonic acids. The addition of chloride promoter prevents the formation of gelatinous products; however, the final product, contains chloride.

The presence of chloride in magnesium sulphonates is a problem from a waste disposal and environmental point of view. When compositions containing such sulphonates are destroyed, e.g. by incineration, harmful chlorinated and polychlorinated biphenyls may be produced. Waste disposal of compositions based on chloride containing sulphonates is therefore a problem; it would be advantageous to be able to produce chloride free magnesium low base number sulphonates especially those derived from high molecular weight sulphonic acids without a loss of the beneficial properties associated with the use of chloride in their manufacture.

In addition to the above mentioned problems, low base number sulphonates have also been found to sensitise the skin, which may lead to dermatological problems for those exposed to them during handling, or to requirements for specific handling. This tendency of a material to be a skin sensitiser is determined by skin patch testing.

Thus, a need exists for magnesium low base number sulphonates, and methods for making such sulphonates, which do not have the foregoing problems of high levels of chloride ions, high viscosity and sediment, high levels of free hydroxyl ion and skinning, and which do not display skin sensitisation problems.

Furthermore, a need exists for lubricating oil formulations which have low levels of phosphorus because it may contaminate automobile catalytic converters and poison the catalytic material. One of the most significant sources of phosphorus in lubricating oils are antiwear agents such as the zinc dialkyldithiophosphates. However, it is difficult to formulate with reduced levels of such antiwear agents and improve or maintain acceptable antiwear properties.

According to the present invention there is provided a method for the preparation of a magnesium low base number sulphonate composition which comprises neutralising a sulphonic acid, or partially neutralised soap thereof, and a carboxylic acid, with a high base number sulphonate.

In a further aspect the invention also provides a magnesium low base number sulphonate composition comprising from at least 10%, preferably at least 20%, by weight of at least one high molecular weight sulphonate, a metal carboxylate and diluent, wherein the sulphonate composition is low in halide ions and has a viscosity of 1000 cS or less at 100° C.

It is preferred that the magnesium low base number sulphonate compositions comprise 20 to 80 wt %, preferably at least 40% and most preferably 40 to 60% by weight of metal sulphonate.

It is also preferred that the kinematic viscosity of the magnesium low base number sulphonate compositions at 100° C. is 700 cS or less e.g. 300 cS or less preferably 150 cS or less and most preferably in the range 30–100 cS (1 cS=$10^{-6} m^2 s^{-1}$).

"Low in halide ions" means having a chloride content of 100 ppm or less, preferably 50 ppm or less and most preferably 20 ppm or less.

The terms "low base number" and "high base number" as used to define sulphonates should be understood in relation to ASTM D2896-88 "Standard Test Method for Base Number of Petroleum Products by Potentiometric Perchloric Acid Titration". This test method is concerned with the determination of basic constituents in petroleum products by potentiometric titration with perchloric acid in glacial acetic acid. The result of this test method is quoted as a base number which is the base equivalence in mg KOH $g^{-1}$. Thus the term "low base number" refers to numerical values of base number which are less than 50 mg KOH $g^{-1}$ and the term "high base number" refers to numerical values of base number which are greater than 50 mg KOH $g^{-1}$ and may be as high as 400 mg KOH $g^{-1}$ or even higher e.g. 600. A sulphonate is neutral if no basic or acidic constituents can be detected by titration.

The magnesium low base number sulphonates of the present invention may be prepared from low molecular weight sulphonic acids, high molecular weight sulphonic acids and mixtures thereof. It is preferred that they are prepared from high molecular weight sulphonic acids.

"High molecular weight sulphonate" means a sulphonate which has been prepared from the neutralisation of a high molecular weight sulphonic acid as defined hereinbelow.

"High molecular weight sulphonic acid" means having a number average molecular weight of 500 or greater, preferably 600 or greater, being an oil soluble synthetic sulphonic acid, which may be an alkyl sulphonic acid, or an alkaryl sulphonic acid. The high molecular weight sulphonic acid may be a single high molecular weight sulphonic acid or it may be a mixture of different sulphonic acids, ie a mixed sulphonic acid. The mixed sulphonic acid may be a mixture of high molecular weight sulphonic acids; that is sulphonic acids which have a number average molecular weight of 500 or greater preferably 600 or greater. The mixed sulphonic acid may be a mixture of high molecular weight sulphonic acid or acids, with lower molecular weight sulphonic acid or acids which have a number average molecular weight of less than 500. When the mixture is a mixture of high molecular weight sulphonic acid or acids and low molecular weight sulphonic acid or acids the proportion by mass of high molecular weight sulphonic acid in the mixture is at least 50%, 60% and most preferably 75%, or is such that the number average molecular weight of the mixture is 500 or greater and most preferably is 600 or greater. Number average molecular weight may be determined by available techniques such as that described in ASTM D-3712.

It is preferred that the high molecular weight sulphonic acid is an alkaryl sulphonic acid such as for example an alkyl benzene sulphonic acid, alkyl toluene sulphonic acid or alkyl xylene sulphonic acid. It is also preferred that it is a mixed sulphonic acid of $C_{15}$ to $C_{60+}$ alkyl benzene or $C_{15}$ to $C_{60+}$, alkyl xylene or $C_{15}$ to $C_{60+}$, alkyl toluene sulphonic acids or mixtures of these.

When a lower molecular weight sulphonic acid is used or is present, it is preferably an alkaryl sulphonic acid and most preferably a mixture of $C_9$ to $C_{30+}$ alkyl substituted alkyl benzene or alkyl toluene or alkyl xylene sulphonic acid. The alkyl may be branched or straight chain. It is preferred that the lower molecular weight sulphonic acid has a number average molecular weight of at least 300, preferably at least 350 and most preferably at least 440. When low molecular weight sulphonic acids are employed in conjunction with a high molecular weight sulphonic acid, it is preferred that their use is kept to a minimum to avoid skin sensitisation which is believed to originate from the low molecular weight sulphonate derived from these acids.

The preferred high molecular weight sulphonic acids and when present or used lower molecular weight sulphonic acids are those which are derived from aromatic alkylates prepared from $C_2$, $C_3$ or $C_4$ polyolefins such as polyethylene, polypropylene or polynormal butene. It is most preferred that they are prepared from polynormal butene. It is also possible to prepare straight chain lower molecular weight sulphonic acids from aromatic alkylates prepared from straight chain hydrocarbons such as linear α-olefins.

When the sulphonic acid is a mixed sulphonic acid and is derived from polynormal butene, it is preferred that it has a number average molecular weight of at least 600 and preferably 600 to 700.

The diluent may be any suitable inert non-volatile oleaginous material or mixture of materials such as a mineral or synthetic oil, petroleum oil or it may be a solvent which is miscible with lubricating and fuel oils. If desired the high molecular weight sulphonic acid or mixture of sulphonic acids may be used in diluted form as a solution or dispersion in a diluent such as mineral or synthetic oil, petroleum oil, or any suitable inert oleaginous material or solvent.

The high base number sulphonates used in the method of this invention may be derived from low or high molecular weight sulphonic acids as hereinbefore defined and whose method of manufacture is discussed above. Their function in the present method is to supply some or all of the base needed in the process for the neutralisation of high molecular weight sulphonic acid or partially neutralised soap, to supply a portion of neutralised sulphonic acid for the final magnesium low base number sulphonate product and, importantly, to supply base to react with the added carboxylic acid to produce the required metal carboxylate to provide the required base number for the magnesium low base number sulphonate. The high base number sulphonate may be the source of some or all of any low molecular weight sulphonic acid which is present in the magnesium low base number sulphonates of the present invention. It is preferred that the high base number sulphonate is derived from the same high molecular weight sulphonic acid as used to prepare the magnesium low base number sulphonate of the present invention. It is preferred that the high base number sulphonate has a TBN of 100 or greater and most preferably 200 or greater.

The primary source of base for preparation of the high base number sulphonate or for the preparation of the partially neutralised soap as used in the method of the present invention or for the direct neutralisation of sulphonic acid in the method of the present invention is a magnesium hydroxide or oxide.

The excess base which is present from the high base number sulphonate reacts with the carboxylic acid present producing a carboxylate. Most of the excess base is converted to carboxylate. However, any excess base which does not react will remain as basic carbonate from the high base number sulphonate. As the excess base in the process is derived from the high base number sulphonate and is in the form of basic carbonate there is little or no free hydroxyl present in the final product.

The carboxylic acid is essential to produce low viscosity products. However the selection of suitable carboxylic acids is crucial. Not all carboxylic acids are suitable. Suitable carboxylic acids for this process are those in which the magnesium salts of the acid are at least sparingly water-soluble. These acids may be mono, di-, tri-, or polycarboxylic acids. They may be aliphatic or aromatic or contain heteroatoms such as for example sulphur although carboxylic acids which contain heteroatoms other than oxygen are not preferred. The suitable carboxylic acids may be saturated or unsaturated, ie contain a carbon to carbon double bond. Suitable monocarboxylic acids include linear or branched monocarboxylic acids such as for example formic acid, acetic acid, and propionic acid. Suitable monocarboxylic acids are $C_1$ to $C_{24}$ monocarboxylic acids, preferably $C_1$ to $C_{18}$ monocarboxylic acids. For low viscosity products which do not skin it has been found that the monocarboxylic acids should be $C_8$ or greater, preferably $C_8$ to $C_{24}$, most preferably $C_8$ to $C_{18}$ monocarboxylic acids. Suitable dicarboxylic acids include linear or branched $C_2$ to $C_8$ dicarboxylic acids such as for example oxalic acid, maleic acid, fumaric acid, adipic acid and succinic acid. Suitable tricarboxylic acids include for example citric acid. An example of a suitable sulphur containing acid is thioglycolic acid. Suitable aromatic acids include benzoic acid, phthallic acid and saiicylic acid. A corresponding anhydride or half ester may be used in place of the dicarboxylic acid, e.g. succinic anhydride, phthalic anhydride or maleic anhydride. The preferred acids are dicarboxylic acids or their anhydrides; the most preferred dicarboxylic acid is succinic acid or its anhydride In the process of the present invention the carboxylic acid or anhydride reacts to produce a metal carboxylate which may be colloidally dispersed within the sulphonate soap in the product. In the process of the present invention sufficient high base number sulphonate and the carboxylic acid are used to generate enough metal carboxylate to provide a total base number for the composition of between 0–50 mg KOH $g^{-1}$. most preferably between 0–30 mg KOH $g^{-1}$.

The carboxylic acid, overbased high base number sulphonate and high molecular weight sulphonic acid or soap may be added to the reaction in any order. The high base number sulphonate can be added prior to the carboxylic acid or conversely the carboxylic acid can be added prior to the high base number sulphonate.

In one embodiment of the method of the present invention a magnesium low base number sulphonate can be prepared directly from the neutralisation of the desired high molecular weight sulphonic acid using a high base number sulphonate. In another embodiment the magnesium low base number sulphonate may be prepared from a partially neutralised soap which has been prepared from the reaction of a high molecular weight sulphonic acid and magnesium oxide, hydroxide or similar. This partially neutralised soap is then reacted with a high base number sulphonate without having first been stripped of any solvent and water which may be present. Alternatively the partially neutralised soap is stripped of solvent and water before neutralisation with high base number sulphonate. The extent of neutralisation of the partially neutralised soap is that which is required to accommodate sufficient of the base from the high base number sulphonate in order to result in the final product having a low base number. The exact extent of neutralisation will depend on the base number of the high base number sulphonate and the concentration of reactants. It is preferred that at least 50% of the sulphonic acid groups present in the soap have been neutralised, more preferably at least 90% or greater or 95% or greater. It is preferred that the partial neutralisation of the high molecular weight sulphonic acid be taken to the maximum achievable neutralisation whilst keeping the viscosity of the soap at an acceptable value with a low level of sediment. Acceptable viscosity in relation to soaps is 300 cS or less and more preferably 200 cS or less. As neutralisation is continued to higher levels and approaches completion the viscosity increases to a point, which may be reached at complete neutralisation, where the soap is a solid or semi-solid. It is preferred that the soap is as concentrated as possible and preferably comprises at least 50% by weight of a mixture of sulphonate and unreacted sulphonic acid. A key feature of the method of the present invention is that a high base number sulphonate is used to provide all or some of the base required for neutralisation of the high molecular weight sulphonic acid and to supply the excess base for reaction with carboxylic acid to produce a metal carboxylate. It is the use of a high base number sulphonate coupled with the use of a carboxylic acid which results in the magnesium low base number sulphonates of the present invention having low viscosities.

If in the process of the present invention a high molecular weight sulphonic acid is used as a starting material for neutralisation it is preferred that the sulphonic acid is added to a polar solvent/diluent mixture in which is dispersed the magnesium oxide hydroxide, carbonate or similar necessary for partial neutralisation of the acid to produce the partially neutralised soap in situ. Water is the preferred polar solvent but alcohols such as methanol, ethanol etc. and mixtures of water and alcohol are also suitable. It is preferred that the polar solvent/diluent mixture comprises between 1 and 50% by weight of water, methanol, ethanol or mixtures thereof and more preferably 15 to 35% by weight. The diluent is preferably a substantially neutral mineral oil synthetic oil or petroleum oil.

The polar material reduces the viscosity of the initial polar solvent/diluent mixture and is believed to aid dispersion of magnesium oxide or hydroxide or carbonate or similar and also aid promotion of the neutralisation reaction. It is preferred that the polar solvent/diluent mixture is mixed with a solvent or mixture of solvents prior to the addition of the magnesium oxide or hydroxide or high molecular weight sulphonic acid. Suitable solvents include aliphatic and aromatic solvents and mixtures thereof such as for example heptane, toluene and xylene. Preferred solvents are toluene and mixtures thereof with other solvents. These solvents aid the viscosity reduction and control during the reaction, aid the solubility of high molecular weight sulphonic acids and assist in the removal of water on completion of reaction by forming azeotropes during the stripping stages.

During the process exothermic reactions may occur: the reaction mixture temperature may be allowed to rise, or may be reduced or maintained by cooling. It is preferred that during the neutralisation reaction the temperature is maintained below 100° C., most preferably below 80° C. so that little or no water is lost from the mixture.

During the process a period of heat soaking may be beneficial after the addition of all the sulphonic acid, to allow the neutralisation to be completed before any further additions or process stages. During a heat soaking period it may be beneficial to maintain the temperature of the reaction mixture at a predetermined level. It is preferred that the reaction temperature is increased, e.g. to 70° C. It is preferred that the heat soaking is for a period of at least 30 minutes and most preferably 1 hour.

On completion of the reaction substantially all of the water present in the reaction mixture and also any additional solvent which is present may be removed by stripping. The stripping may be carried out with nitrogen, with increased temperature of the reaction mixture, with gradual application of a vacuum or with a combination of all three.

During the process sediment may be formed which may be removed via filtration. It is preferred that sediment formation is as low as possible so that the amount of filtration required is kept to a minimum and is as fast as possible. During filtration a filter aid may be used, preferably a fine porosity filter aid e.g. diatomaceous earth. Filtration may be carried out at an elevated temperature e.g. at between 150–160° C. and under applied pressure, e.g. 8 bar. A feature of the process of the present invention is that low levels of sediment are produced at completion of the reaction. This allows for the use of a simple polish filtration which reduces the need for filter aids and the subsequent problems associated with waste disposal. The process of the present invention typically produces sediment levels in the final product of 0.6 vol % or less e.g. 0.5 vol % or less and preferably 0.2 vol % or less and most preferably 0.1 vol % or less without filtration.

If desired further additions of diluent may be made in order to obtain a desired final product viscosity, content of basic sulphonate or total base number. Preferably these additions are made after filtration. Additives such as anti-foam agents may be added during the process or after filtration.

The process of the present invention produces magnesium low base number sulphonates which have low viscosity and good fluidity. They have low levels of chlorine because chlorine containing fluidisers as used in prior art processes are not required. It is believed that the resultant products are also non-skin sensitising when high molecular weight sulphonic acids are used in their preparation.

The magnesium low base number sulphonates of the present invention are useful as additives for oil-based compositions, for example, lubricants, and greases. The invention thus also provides such compositions containing the magnesium low base number sulphonates.

The amount of magnesium low base number sulphonate that should be used in the oil based composition depends on the type of composition and its proposed application. Automotive crankcase lubricating oils preferably contain 0.01% to 5 mass % of the magnesium low base number sulphonate, on an active ingredient basis, based on the mass of the oil.

The magnesium low base number sulphonates of the present invention are oil-soluble or (in common with certain of the other additives referred to below) are dissolvable in oil with the aid of a suitable solvent, or are stably dispersible materials. Oil-soluble, dissolvable, or stably dispersible as that terminology is used herein does not necessarily indicate that the materials are soluble, dissolvable, miscible, or capable of being suspended in oil in all proportions. It does mean, however, that the materials are, for instance, soluble or stably dispersible in oil to an extent sufficient to exert their intended effect in the environment in which the oil is employed. Moreover, the additional incorporation of other additives may also permit incorporation of higher levels of a particular additive, if desired.

Additives, including the magnesium low base number sulphonates of the present invention, can be incorporated into a base oil in any convenient way. Thus, they can be added directly to the oil by dispersing or by dissolving them in the oil at the desired level of concentration. Such blending can occur at room temperature or an elevated temperature.

Magnesium low base number sulphonates of the present invention are particularly useful in lubricating oil compositions which employ a base oil in which the mixtures are dissolved or dispersed. Base oils with which the magnesium low base number sulphonates may be used include those suitable for use as crankcase lubricating oils for spark-ignited and compression-ignited internal combustion engines, for example, automobile and truck engines, marine and railroad diesel engines. They may also be used, for example, in base oils suitable for use as aviation lubricants or as lubricants for two cycle engines. They may also be used in a base oil in a wide variety of other applications such as gear oils, automatic transmission fluids, tractor oils, metalworking fluids and anti-corrosion coatings. Suitable base oils may be natural or synthetic.

Synthetic base oils include alkyl esters of dicarboxylic acids, polyglycols and alcohols; poly-α-olefins, including polybutenes; alkyl benzenes; organic esters of phosophoric acids; and polysilicone oils.

Natural base oils include mineral lubricating oils which may vary widely as to their crude source, for example, as to whether they are paraffinic, naphthenic, mixed, or paraffinic naphthenic, as well as to the method used in their production, for example, distillation range, straight run or cracked, hydrofined, solvent extracted and the like.

More specifically, natural lubricating oil base stocks which can be used may be straight mineral lubricating oil or distillates derived from paraffinic, naphthenic, asphaltic, or mixed base crude oils. Alternatively, if desired, various blended oils may be employed as well as residual oils, particularly those from which asphaltic constituents have been removed. The oils may be refined by any suitable method, for example, using acid, alkali, and/or clay or other agents such as, for example, aluminium chloride, or they may be extracted oils produced, for example, by solvent extraction with solvents, for example, phenol, sulphur dioxide, furfural, dichlorodiethyl ether, nitrobenzene, or crotonaldehyde.

The lubricating oil base stock conveniently has a viscosity of about 2.5 to about 12 cS (about $2.5 \times 10^{-6}$ to about $12 \times 10^{-6}$ m$^2$/s) and preferably about 2.5 to about 9 cS (about $2.5 \times 10^{-6}$ to about $9 \times 10^{-6}$ m$^2$/s) at 100° C. Mixtures of synthetic and natural base oils may be used if desired.

The magnesium low base number sulphonates of the present invention may be employed in a lubricating oil composition which comprises lubricating oil, typically in a major proportion, and the sulphonates, typically in a minor proportion, for example, in a proportion as indicated above. Additional additives may be incorporated in the composition to enable it to meet particular requirements. Examples of additives which may be included in lubricating oil compositions are other detergents and metal rust inhibitors, viscosity index improves, corrosion inhibitors, oxidation inhibitors, friction modifiers, dispersants, anti-foaming agents, anti-wear agents, pour point depressants, and rust inhibitors. Such additives are well known in the art.

Some of these additives can provide a multiplicity of effects; thus for example, a single additive may act as a dispersant-oxidation inhibitor as known in the art.

Compositions when containing the above-mentioned additives are typically blended into the base oil in amounts which are effective to provide their normal function. Representative effective amounts of such additives, if present, are illustrated as follows:

| Additive | Mass % a.i.* (Broad) | Mass % a.i.* (Preferred) |
|---|---|---|
| Detergents/Rust Inhibitors | 0.01–6 | 0.01–4 |
| Viscosity Modifier | 0.01–6 | 0.01–4 |
| Corrosion Inhibitor | 0.01–5 | 0.01–1.5 |
| Oxidation Inhibitor | 0.01–5 | 0.01–1.5 |
| Dispersant | 0.1–20 | 0.1–8 |
| Pour Point Depressant | 0.01–5 | 0.01–1.5 |
| Anti-foaming Agent | 0.001–3 | 0.001–0.15 |
| Anti-wear Agents | 0.01–6 | 0.01–4 |
| Friction Modifier | 0.01–5 | 0.01–1.5 |
| Mineral or Synthetic Base Oil | Balance | Balance |

*Mass % active ingredient based on the final oil

When a plurality of additives is employed, it may be desirable, although not essential, to prepare additive concentrates comprising the additives (the concentrate being referred to herein as an additive package) whereby several additives can be added simultaneously to the base oil to form the lubricating oil composition. Dissolution of the additive concentrate into the lubricating oil may be facilitated, for example, by mixing accompanied with heating, but this is not essential. The concentrate or additive package will typically be formulated to contain the additive(s) in amounts to provide the desired concentration in the final formulation when the additive package is combined with a predetermined amount of base lubricant. Thus, one or more magnesium low base number sulphonates prepared in accordance with the present invention can be added to small amounts of base oil or other compatible solvents along with other desirable additives to form additive packages containing active ingredients in an amount, based on the additive package, of, for example, from about 2.5 to about 90 mass %, and preferably from about 5 to about 75 mass %, and most preferably from about 8 to about 50 mass % by weight, additives in the appropriate proportions with the remainder being base oil.

The final formulations may employ typically about 10 mass % of the additive- package, the remainder being base oil.

The present invention therefore further provides a lubricating oil composition which comprises a major amount of a lubricating oil and a minor amount of a magnesium low base number sulphonate composition according to the present invention. Such a lubricating oil composition may be a low phosphorus composition, ie have a phosphorus content of 0.1 wt % or less, preferably 0.08 wt % or less and most preferably 0.05 wt % or less.

The present invention also provides a lubricating oil concentrate which comprises a magnesium low base number sulphonate composition according to the present invention and one or more other lubricant additives.

The magnesium low base number sulphonate compositions of the present invention have been found to provide improved wear performance, particularly preferred being those which contain one of formate, fumarate, succinate, maleate, citrate or adipate, most preferably fumarate, maleate, succinate or citrate, it being most preferred that the composition has a TBN of less than 24, preferably in the range of 5 to 24.

The invention is further illustrated by way of example only with reference to the following Examples.

Manufacture of Magnesium low Base Number Sulphonate (COMPARATIVE EXAMPLE)

Diluent oil (256 g) and water (110 g) were mixed in a reaction vessel. Magnesium oxide of greater than 95% purity (21)g was added to the water/diluent mixture and the temperature adjusted to 25 to 35° C. Formic acid solution (18 g) was added to the reaction vessel, the resulting temperature rise limited, by cooling, to approx. 37° C. A mixed low molecular weight sulphonic acid made up of $C_{24}$ average alkyl benzene sulphonic acid and a $C_{12}$ average alkyl xylene sulphonic acid of number average molecular weight 440 as an approximately 70% by mass solution in diluent oil (314 g) was added to the reaction vessel and the resulting temperature rise controlled by cooling to limit the temperature to 60–70° C. The reaction mixture was stabilised at this temperature for 1 hour. A further addition of magnesium oxide (11 g) was then added to the reaction mixture with stirring followed by a further addition of sulphonic acid (314 g); the resulting temperature rise was controlled by cooling to limit the temperature to 80° C. The reaction mixture was stabilised at this temperature for 1 hour. The reaction mixture was then heated from 80–110° C. linearly over a period of 4 hours. The reaction mixture was then heated to 160° C. linearly over a period of 2 hours in order to strip water from the mixture utilising a purge. At 150° C. the pressure was reduced to 400 mbar absolute over a period of 25 minutes and then the reaction mixture was maintained at 160° C. for a further 30 minutes. A diatomaceous filter aid (2.5% by mass) was added to the stripped reaction product which was then filtered. A further 51.53 g of diluent oil was added to the filtered product to produce the final product.

After the vacuum stripping, this product had a sediment volume of 1.0 %, a viscosity of 720 cS at 100° C., a TBN Of 24 and a soap content of 48 mass %. Sediment volume was measured by removing a sample (50 ml) from the reactor and dissolving in toluene (50 ml). The mixture was then added to a 100 ml calibrated centrifuge tube. The solution was then centrifuged for 20 minutes at 1500 rpm and the volume of sediment in the tube measured. This example illustrates that attempted preparation of a magnesium low base number sulphonate using a conventional process produces a sub standard product which has high viscosity and sediment levels.

Preparation of High Base Number Sulphonate 524 g of toluene and 438 g (0.63 moles) of a 69 mass % solution of an alkyl benzene sulphonic acid (molecular weight 480) were added to a 2 litre glass reactor fitted with stirrer, reflux condenser, a gas distribution tube and temperature control. This mixture was heated to 22° C. when 24 g of methanol was added. There was an immediate exotherm, as a result of which the temperature of the mixture rose to 24° C. 185.7 g (4.60 moles) of magnesium oxide was then added. There was a rapid exotherm to 36° C. as the sulphonic acid was neutralised. 68.6 g of ethylene diamine carbonate solution, comprising 35.5 mass % water, 35.5 mass % methanol, 16.8 mass % ethylene diamine and 12.2 mass % carbon dioxide was then added as reaction promoter. A further 49.7 g of methanol and 130.5 g of water was then added. The temperature of the mixture was brought to 46° C. and carbon dioxide injected into the reaction mixture at a rate of 49.6 g/hour.

During carbonation the temperature of the carbonation mixture was allowed to follow its natural course and slowly increased to about 65° C. and then fell again as the reaction subsided as the magnesium oxide was consumed. When the temperature had fallen to 60° C., heat was applied, and the temperature was maintained at 60° C. until carbonation was complete. When 166 g of carbon dioxide had been injected into the carbonation mixture, the apparatus was changed from a reflux to distillation configuration. Carbonation was continued until 210.8 g of carbon dioxide had been passed into the reaction mixture.

On completion of the carbonation, a sample was removed from the reaction mixture and centrifuged. There was 0.6 vol % of sediment in the sample as determined under the conditions described in the comparative Example above.

While maintaining the temperature of the mixture at 60° C., 213.3 g of diluent oil, also at 60° C., were added, and the mixture so obtained was distilled at atmospheric pressure to 165° C. whilst introducing a stream of nitrogen. When the distillation temperature reached 165° C., a vacuum of 200 mbar was applied, and maintained for 105 minutes to remove the last traces of water, methanol and toluene. After releasing the vacuum, a 50 cm$^3$ sample was removed from the stripped mixture and dissolved in 50 cm$^3$ of toluene. The diluted sample was centrifuged to show that 1.0 vol % of sediment (PCS) remained in the stripped mixture. 8 g of filter aid was then added to the stripped mixture in the reactor and the mixture so obtained was filtered through a pressure filter preheated to 160° C. and containing 5 g of filter aid as precoat. The filtration rate was 450 Kg/m$^2$/hr. The filtered product was bright and clear with a TBN of 422 mg KOH/g. Diluent oil (4.2 g/100 g of filter product) was blended into the filtered material at 100° C. The final product had a TBN of 405 mg KOH/g.

The total amount of methanol in the system (including the methanol used in the neutralisation step and that in the promoter solution) was 98.0 g. The total amount of water in the system (including the water in the promoter solution) was 154.9 g. This process was repeated for a sulphonic acid of average molecular weight 680. The resultant products were high base number magnesium sulphonates whose properties are illustrated in Table 1.

TABLE 1

| High Base Number Sulphonate | 1 | 2 |
|---|---|---|
| Sulphonic Acid | Low molecular weight | High Molecular weight |
| Mn of Sulphonic Acid | 490 | 680 |
| TBN mg KOH g$^{-1}$ | 405 | 400 |

EXAMPLE 1: Preparation Directly from Sulphonic Acid

5 Toluene (303 g) water (54 g) and diluent oil (264 g) were charged to a reaction vessel and were mixed at 400 rpm. To this mixture was charged magnesium hydroxide (11.2 g). The temperature of the reaction mixture was adjusted to approximately 50° C. To this reaction mixture was added a $C_{15}$–$C_{60+}$alkyl sulphonic acid of number average molecular weight 670 as a 60% by mass solution in diluent oil (696 g) over a period of 15 minutes; on completion of this addition the temperature of the reaction mixture was adjusted to 70° C. The reaction mixture was held at this temperature for 1 hour, this being a heat soaking period. On completion of this heat soaking period 100 ppm of antifoamant (based on the total reactor charge) was added. Then succinic acid (10.1 g) was added to the reaction mixture and the reaction mixture was held at 70° C. for 15 minutes. To this reaction mixture high base number sulphonate as prepared above (39 g) was added over 5 minutes. After this the reaction mixture was stripped with $N_2$ (100 ml min$^{-1}$) with a temperature rise from 70° C. to 160° C. in 1 hour with a final vacuum strip (553 mm Hg) for 30 minutes at 160° C. The product was then filtered using 0.5% by mass of a diatomaceous filter aid.

The resultant product had an end of process sediment level of 0.1 vol %, a kinematic viscosity at 100° C. of 39 cS, a TBN of 11 and a soap content of 43.5 mass %. The product was calculated to contain about 15 ppm by weight of chlorine.

EXAMPLES 2 to 13

The method of Example 1 was repeated for a number of different high base number sulphonates and carboxylic acids. The results are provided in Table 2 along with details of process variations. Example 10 was found to have low skinning on exposure to air.

TABLE 2

| Example No. | 2 | 3 | 4 | 5 | 6 | 7 |
|---|---|---|---|---|---|---|
| Carboxylic Acid | Formic Acid | Succinic Acid added before HBNS | Succinic Acid | Succinic Acid added before HBNS | Fumaric Acid | Succinic Acid |
| Carboxylic Acid, g | 8.1 | 10.1 | 10.1 | 14.3 | 10.1 | 10.1 |
| Toluene, g | 404 | 303 | 303 | 303 | 303 | 303 |
| Water, g | 46.3 | 54 | 54 | 54 | 54 | 54 |
| Oil, g | 254 | 264 | 264 | 288 | 264 | 360 |
| Sulphonic Acid, Mn | 670 PNB | 680 | 680 PNB | 88% Al | 680 | MW = 490 69% Al |
| Sulphonic Acid (60% Al), g | 694 | 696 | 696 | 650 | 696 | 600 |
| HBNS | 1 | 1 | 2 | 2 | 1 | 1 |
| HBNS, g | 34.8 | 39 | 39.8 | 56 | 39 | 40.8 |
| MgO, g | 11.7 | 11.2 | 11.2 | 15.5 | 11.2 | 15.2 |
| Soap, mass % | 43.5 | 43.5 | 43.5 | 60 | 43.5 | 43.5 |
| JBN, mg KOH/g | 10.6 | 11 | 12.3 | 15.2 | 11 | 10 |
| Hep. Sed., vol % | 0.04 end of process | 0.10 end of process | 0.06 end of process | 0.08 end of process | 0.06 end of process | 0.08 end of process |

TABLE 2-continued

| Kinematic Viscosity at 100° C., cS | 45 | 39 | 39 | 198 | 39 | 35.8 |
|---|---|---|---|---|---|---|
| Example No. | 8 | 9 | 10 | 11 | 12 | 13 |
| Carboxylic Acid | Citric Acid 1H2O | Phthalic Anhydride | Octanoic Acid | Succinic Acid | Oleic Acid | Benzoic Acid |
| Carboxylic Acid g | 11.8 | 12.9 | 24.7 | 10.1 | 48 | 21 |
| Toluene g | 303 | 303 | 303 | 303 | 303 | 303 |
| Water g | 54 | 54 | 54 | 54 | 54 | 54 |
| Oil g | 264 | 264 | 264 | 360 | 264 | 264 |
| Sulphonic Acid Mn | 680 | 680 | 680 | MW = 440 69% Al | 680 | 680 |
| Sulphonic Acid g | 696 | 696 | 696 | 600 | 696 | 696 |
| HBNS | 1 | 1 | 1 | 1 | 1 | 1 |
| HBNS g | 39 | 39 | 39 | 42.6 | 39 | 39 |
| MgO g | 11.2 | 11.2 | 11.2 | 17.3 | 11.2 | 11.2 |
| Soap mass % | 43.5 | 43.5 | 43.5 | solid | 43.5 | 43.5 |
| TBN mg KOH/g | 8.3 | 10.8 | 11.6 | solid | 11.4 | 11.8 |
| Hep. Sed. vol % | 0.2 end of process | 0.04 end of process | 0.03 end of process | solid | 0.04 end of process | 0.03 end of process |
| Viscosity at 100° C. cS | 41.6 | 299 | 55.9 | Solid | 49.6 | 42.9 |

Wear Performance

A magnesium low base number sulphonate was evaluated for its wear performance using a SMIRA Valve Train Wear Rig; this apparatus is described in test method CEC L-31-T-81. The version used in this evaluation was a monocam rig. which describes a Cam and Follower Test Machine. The following three temperature test protocols were used:

TABLE 3

| Oil Temperature ° C. | Cam Speed RPM | Time Mins. | Load Kg |
|---|---|---|---|
| 40 | 250 | 30 | 20 |
|  |  | +60 | 60 |
| 65 | 1500 | 30 | 20 |
|  |  | +60 | 60 |
| 120 | 1500 | 30 | 20 |
|  |  | +60 | 60 |

Two lubricating oil formulations were evaluated.

Formulation 1 was prepared in mineral basestock using conventional viscosity modifier, dispersant a proprietary detergent package, a mixture of antioxidants including a ZDDP. Formulation 2 was prepared in a mixed mineral and synthetic basestock using the same additives as Formulation 1 but with the addition of an aromatic amine antioxidant and an additional ZDDP thus providing a formulation with a mixture of ZDDP's. In each Formulation the magnesium low base number sulphonate was evaluated at a concentration of 0.9 wt % based on weight of the formulation.

Oil performance was evaluated in terms of tappet wear in microns at the end of the test. The results are shown in Table 4. A negative value for Δ indicates an improved wear performance relative to no low base number sulphonate in the formulation.

TABLE 4

|  |  | Formulation 1 | | | | Formulation 2 | | | | |
|---|---|---|---|---|---|---|---|---|---|---|
|  |  | 65 DEG | | 120 DEG | | 40 DEG | | 65 DEG | | 120 DEG | |
| Test No. | LBNS | Cam Wear | Δ | Cam Wear | Δ | Cam Wear | Δ | Cam Wear | Δ | Cam Wear | Δ |
| 1 | No LBNS | 5.14 | — | 8.07 | — | 2.57 | — | 6.57 | — | 10.71 | — |
| 2 | Mg LBNS Succinate | 6.40 | 1.26 | 6.10 | −1.97 | 3.00 | 0.43 | 4.90 | −1.67 | 6.70 | −4.01 |

We claim:

1. A magnesium low base number sulphonate composition comprising from at least 10% by weight of at least one sulphonate, a magnesium carboxylate and diluent, wherein the sulphonate composition has a chloride content of 100 ppm by weight or less and a viscosity of 700 cS or less at 100° C., wherein the low base number is a numerical value of base numbers less than 50 mg KOH g-1.

2. A magnesium low base number sulphonate composition as claimed in claim 1 wherein the composition comprises at least 40% by weight of sulphonate.

3. A magnesium low base number sulphonate composition as claimed in claim 1 wherein the sulphonate is prepared from neutralisation of a sulphonic acid having a number average molecular weight of 500 or greater, being an oil-soluble synthetic sulphonic acid or an alkaryl sulphonic acid.

4. A magnesium low base number sulphonate as claimed in claim 3 wherein the sulphonic acid has a number average molecular weight of 600 or greater.

5. A magnesium low base number sulphonate composition as claimed in claim 1 wherein the sulphonate is derived from a $C_{15}$ to $C_{60+}$alkyl substituted alkaryl sulphonic acid.

6. A magnesium low base number sulphonate composition as claimed in claim 5 wherein the sulphonate is derived from a sulphonic acid which has alkyl substitution derived from poly (normal butene) polymers.

7. A lubricating oil composition which comprises a major amount of a lubricating oil and a minor amount of a magnesium low base number sulphonate composition as claimed in claim 1.

8. The composition of claim 7 having a phosphorus content of 0.1 wt % or less.

9. A lubricating oil concentrate which comprises a magnesium low base number sulphonate composition as claimed in any of claims 1 to 6 and one or more other lubricant additives.

10. A magnesium low base number sulphonate composition as claimed in claim 1 wherein the sulphonate composition has a viscosity of 300 cS or less at 100° C.

* * * * *